United States Patent
Ozminkowski, Jr.

(10) Patent No.: US 10,602,711 B2
(45) Date of Patent: Mar. 31, 2020

(54) HYBRID TOMATO VARIETY 'H1776'

(71) Applicant: H.J. Heinz Company Brands LLC, Pittsburgh, PA (US)

(72) Inventor: Richard Henry Ozminkowski, Jr., Lodi, CA (US)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 1 day.

(21) Appl. No.: 15/974,835

(22) Filed: May 9, 2018

(65) Prior Publication Data

US 2019/0343064 A1    Nov. 14, 2019

(51) Int. Cl.
*A01H 5/08* (2018.01)
*A01H 6/82* (2018.01)
*A01H 1/00* (2006.01)

(52) U.S. Cl.
CPC ............... *A01H 6/825* (2018.05); *A01H 1/00* (2013.01); *A01H 5/08* (2013.01)

(58) Field of Classification Search
None
See application file for complete search history.

(56) References Cited

U.S. PATENT DOCUMENTS 8,957,287 B2 *   2/2015   Bunn .................... A01G 22/00
                                                      800/317.4

* cited by examiner

*Primary Examiner* — Phuong T Bui
(74) *Attorney, Agent, or Firm* — Fitch, Even, Tabin & Flannery LLP

(57) ABSTRACT

Hybrid tomato variety 'H1776' is described. The tomato variety is a ground-culture hybrid tomato variety suitable for machine harvest, and is adaptable to the climactic conditions of regions such as California (USA), Portugal, and Spain.

21 Claims, 3 Drawing Sheets
(3 of 3 Drawing Sheet(s) Filed in Color)

HYBRID TOMATO VARIETY 'H1776'

FIELD

This disclosure relates to the field of plant breeding. In particular, this disclosure relates to a new variety of tomato, *Solanum lycopersicum* variety denominated 'H1776'.

BACKGROUND

Breeding improved tomato varieties involves providing genetics that give an advantage to the grower, processor, consumer, or other member of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining resistance to *Verticillium* wilt race 1 (*Verticillium dahliae*), *Fusarium* wilt race 1 and 2 (*Fusarium oxysporum* pv *lycopersici*), and root knot nematode (*Meloidogyne incognita*) are highly desirable in most climates around the world.

Moreover, in regions such as California, the industry has seen a considerable increase in pressure from tomato spotted wilt virus (TSWV). Thus, varieties with resistance to TSWV are in high demand by both growers and processors to ensure a productive crop cycle, particularly those with high field yield.

However, to be commercially viable, the tomato variety must perform acceptably in the field and factory as required by any other processing tomato variety.

Processing tomato quality parameters differ from those of fruit used in the fresh market. The processing characteristics are typically determined using a sample of hot-break tomato pulp or juice produced in a consistent manner to those familiar with the art. For example, a fixed mass of tomatoes may be cooked in a microwave oven for several minutes to halt any enzymatic breakdown of the sample, lost water is replaced, and the sample is pulped to remove skins and seed to produce a uniform juice sample. The juice sample can be analyzed for various quality parameters important to processing tomato including but not limited to gross viscosity measures such as juice Bostwick, soluble solids measures using a refractometer (°Brix), measures of acidity and pH, and measures of color for example a Hunter a/b score. The value of these traits depends on the product that is being commercially produced by the processing factory. In some instances, a factory will put a higher value on a thick viscosity variety, whereas in other instances, a thin viscosity will make a superior product.

SUMMARY

Provided herein is a new and distinct tomato variety named 'H1776' that produces excellent yields of large uniform fruit. It demonstrates adaptability to several arid tomato production regions around the world, in particular the central valley of California. The yield advantage of 'H1776' is strengthened by resistance to tomato spotted wilt virus. 'H1776' has demonstrated a very vigorous vine and strong yields relative to the industry check 'H5608'. The variety 'H1776' has resistance to *Verticillium* wilt race 1, *Fusarium* wilt races 1 and 2, southern root knot nematode, bacterial speck race 0, and tomato spotted wilt virus (TSWV). The fruit of 'H1776' are medium-large and of blocky-oval shape, have very good internal color, are very firm, and have an average fruit weight of 83 grams. 'H1776' presents an advantage over the industry standard variety 'H5608' because of its fruit size and improved soluble solids. The juice of 'H1776' also has a thicker viscosity than 'H5608' as measured both by its gross viscosity (Bostwick) and its serum viscosity (centistokes). Tolerance to fruit rot in 'H1776' is good, allowing for once-over machine harvesting applications and it is considered an extended field storage (EFS) variety; however, in Ontario, Canada trial there was some fruit cracking.

In one aspect, the present disclosure is directed to tomato seed designated as 'H1776' having ATCC Accession Number PTA-124677. In another aspect, the present disclosure is directed to a tomato plant, as well as any plant part or portion isolated therefrom, produced by growing 'H1776' tomato seed. In at least one approach, the plant part includes at least one cell from tomato variety 'H1776'. In another aspect, the present disclosure is directed to a tomato plant or part isolated therefrom having all the physiological, morphological, and/or genetic characteristics of a tomato plant produced by growing 'H1776' tomato seed having ATCC Accession Number PTA-124677. In yet another aspect, the present disclosure is directed to a tomato plant having all of the characteristics of tomato variety 'H1776' listed in Table 1 below, wherein representative seed is deposited under ATCC Accession Number PTA-124677.

In still another aspect, the present disclosure is directed to tomato seed having at least a first set of the chromosomes of tomato variety 'H1776', wherein representative seed is deposited under ATCC Accession Number PTA-124677. In still another aspect, the present disclosure is directed to an $F_1$ hybrid tomato seed, plants grown from the seed, and leaves, ovules, pollen, rootstocks, scions, fruit, cotyledons, embryos, meristems, anthers, roots, root tips, pistils, flowers, stems, calli, stalks, hypocotyla, pericarps, or portion thereof isolated therefrom having 'H1776' as a parent, wherein 'H1776' is grown from 'H1776' tomato seed having ATCC Accession Number PTA-124677. The disclosure is also directed to a method of producing a tomato plant derived from tomato variety 'H1776', including crossing a plant of tomato variety 'H1776' with another tomato plant. The method may further comprise harvesting seed from the $F_1$ hybrid tomato seed and/or crossing the $F_1$ hybrid tomato plant with itself or another plant to produce seed from a progeny plant.

Tomato plant parts include leaves, ovules, pollen, cells fruit, cotyledons, embryos, meristems, anthers, roots, root tips, pistils, flowers, stems, calli, stalks, hypocotyla, pericarps, the like, and any portion thereof. In one aspect, the plant part includes at least one cell from tomato variety 'H1766'. In another embodiment, the present invention is further directed to tomato fruit, stems, leaves, parts of leaves, roots, root tips, pollen, ovules, cells, scion, rootstock, seeds, and flowers isolated from 'H1776' tomato plants. In another aspect, the present disclosure is further directed to tissue culture of regenerable cells derived from 'H1776' tomato plants. The disclosure is further directed to a tomato plant regenerated from tissue culture. In another aspect, the disclosure is directed to a protoplast produced from tissue culture and a plant regenerated from the protoplast. At least in some approaches, the plant regenerated from the tissue culture or protoplast has all of the physiological and morphological characteristics of tomato variety 'H1776' listed in Table 1.

In another aspect, the disclosure is directed to a method for producing a plant part, which at least in one aspect is tomato fruit, and harvesting the plant part. The disclosure also is directed to vegetatively propagating a plant of tomato variety 'H1776' by obtaining a part of the plant and regenerating a plant from the plant part. At least in some approaches, the regenerated plant has all of the physiological and morphological characteristics of tomato variety 'H1776' listed in Table 1.

In yet another aspect, the present disclosure is further directed to a method of selecting tomato plants by a) growing 'H1776' tomato plants wherein the 'H1776' plants are grown from tomato seed having ATCC Accession Number PTA-124677; and b) selecting a plant from step a). In another aspect, the present invention is further directed to tomato plants, plant parts, and seeds produced by the tomato plants, where the tomato plants are isolated by the selection method.

In another aspect, the present invention is further directed to a method of breeding tomato plants by crossing a tomato plant with a plant grown from 'H1776' tomato seed having ATCC Accession Number PTA-124677. In still another aspect, the present disclosure is further directed to tomato plants, tomato parts from the tomato plants, and seeds produced therefrom where the tomato plant is isolated by the breeding method.

In another aspect, the disclosure relates to a plant of tomato variety 'H1776' comprising a transgene and/or a single locus conversion, and any seeds or plant parts isolated therefrom. The disclosure also relates to methods for preparing a plant of tomato variety 'H1776' comprising a transgene and/or a single locus conversion.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
FIG. 1 illustrates characteristics of the 'H1776' plant.
Figure 2:
FIG. 2 illustrates external fruit and plant characteristics of 'H1776'.
Figure 3:
FIG. 3 illustrates internal fruit characteristics of 'H1776'.

Described herein is a new and distinct tomato variety named 'H1776' that was developed to provide ground-culture hybrid tomato varieties (i.e., not grown on stakes) that are suitable for machine harvest, and is adaptable to the climatic conditions of regions such as California, USA; Portugal; and Spain.

Tomato plants of 'H1776' are resistant to *verticillium* wilt race 1, *fusarium* wilt races 1 and 2, southern root knot nematode, bacterial speck, and tomato spotted wilt virus. Plants are medium green in color with a large, sprawling habit as compared to tomato varieties of the same market class. Fruit of 'H1776' are large (83 gram) for a processing variety, very firm, with a thick pericarp. These fruit qualities make 'H1776' a variety suitable for peeling and dicing.

Stability of Variety 'H1776'

The variety is uniform and stable within commercially acceptable limits. As is true with other tomato varieties, a small percentage of variants can occur within commercially acceptable limits for almost any characteristic during the course of repeated multiplication. However, no variants were observed during the two years in which the variety was observed to be uniform and stable.

TABLE 1

Characterization of tomato variety 'H1776' compared to an industry standard, 'H5608'

| Character | H1776 | H5608 |
|---|---|---|
| Seedling | | |
| Anthocyanin in hypocotyl: | Present | Present |
| Habit of 3-4 week old seedling: | Normal | Normal |
| Mature Plant | | |
| Height (cm): | 48 | 52 |
| Growth Type: | Determinate | Determinate |
| Form: | Normal | Sprawling |
| Size of Canopy: | Large | Large |
| Habit: | Sprawling | Sprawling |
| Stem | | |
| Branching: | Profuse | Profuse |
| Branching at Cotyledon: | Absent | Absent |
| # nodes below first inflorescence: | 4-7 nodes | 4-7 nodes |
| # nodes between early inflorescence: ($1st-2^{nd}$, $2^{nd}$-3rd) | 1-2 nodes | 1-2 nodes |
| # nodes between later inflorescence | 1-2 nodes | 1-2 nodes |
| Pubescence on younger stems: | Moderate | Sparse |
| Leaf | | |
| Type: | Tomato | Tomato |
| Morphology: | Compound with major and minor leaflets | Compound with major and minor leaflets |
| Margins of Major Leaflets: | Shallowly toothed/scalloped | Shallowly toothed/scalloped |
| Marginal Rolling or Wiltness: | Slight | Moderate |
| Onset of Leaflet Rolling: | Midseason | Midseason |
| Surface of Major Leaflets: | Rugose | Rugose |
| Pubescence | Normal | Normal |
| Inflorescence | | |
| Type: | Forked | Forked |
| # flowers in inflorescence average: | 6 | 6 |
| leafy or "running" inflorescence: | Absent | Absent |
| Flower | | |
| Calyx: | Normal | Normal |
| Calyx-Lobes: | Shorter than corolla | Shorter than corolla |
| Corolla Color: | Yellow | Yellow |
| Style pubescence: | Sparse | Sparse |
| Anthers: | Fused/Tubed | Fused/Tubed |
| Fasciation: | Absent | Absent |
| 1st flower of 2nd or 3rd Inflorescence: | Absent | Absent |
| Fruit | | |
| Typical shape in longitudinal section: | Blocky oval | Blocky oval |
| Shape of transverse section: | Round | Round |
| Shape of stem end: | Indented | Indented |
| Shape of blossom end: | Flat | Flat |
| Shape of pistil scar: | stellate | Dot |
| Abscission layer: | Absent | Absent |
| Point of detachment fruit at harvest: | At calyx | At calyx |
| Length of pedicel (joint to calyx attachment) (cm): | n/a | n/a |

TABLE 1-continued

Characterization of tomato variety 'H1776' compared to an industry standard, 'H5608'

| Character | H1776 | H5608 |
|---|---|---|
| Length of mature fruit (cm) (stem axis) (cm): | 6.0 | 5.7 |
| Diameter of fruit at widest point (cm): | 4.8 | 4.2 |
| Weight of Mature Fruit (g): | 74 | 50 |
| Number of Locules | 3-4 | 2-4 |
| Fruit Surface: | Smooth | Smooth |
| Fruit Base Color (mature green) (Mature Green Stage): | Light green | Yellow green |
| Fruit Pattern (mature green stage) | Uniform | Uniform |
| Shoulder color if different from base | n/a | n/a |
| Fruit color full ripe: | Red | Red |
| Flesh color full ripe: | Red | Red |
| Flesh color: | Uniform | Uniform |
| Locular gel color of table-ripe fruit | Red | Yellow |
| Ripening: | Uniform | Uniform |
| Ripening: | Uniformly | Uniformly |
| Stem Scar Size: | Small | small |
| Core: | Present | Present |
| Epidermis Color: | Yellow | Yellow |
| Epidermis: | Normal | Normal |
| Epidermis Texture: | Average | Tough |
| Thickness or Pericarp (mm): | 7.5 | 6.5 |
| Resistance to Fruit Disorder: | Not tested | Not tested |
| Disease and Pest Reactions | | |
| Viral Diseases | | |
| Cucumber Mosaic: | n/t | n/t |
| Curly Top: | n/t | n/t |
| Potato-y Virus: | n/t | n/t |
| Blotch Ripening: | n/t | n/t |
| Tobacco Mosaic Race 0: | n/t | n/t |
| Tobacco Mosaic Race 1: | n/t | n/t |
| Tobacco Mosaic Race 2: | n/t | n/t |
| Cracking, Concentric: | n/t | n/t |
| Tobacco Mosaic Race $2^2$: | n/t | n/t |
| Tomato Spotted Wilt: | resistant | resistant |
| Tomato Yellows: | n/t | n/t |
| Gold Fleck: | n/t | n/t |
| Others: | n/t | n/t |
| Bacterial Disease | | |
| Bacterial Canker (*Clavibacter michiganense*): | Susceptible | susceptible |
| Bacterial Soft Rot (*Erwinia corotovora*): | n/t | n/t |
| Bacteria Speck (*Pseudomonas tomato*): | Resistant | Resistant |
| Bacterial Spot (*Xanthomonas* spp): | Susceptible | susceptible |
| Bacterial Wilt (*Ralstonia solancearum*): | n/t | n/t |
| Other Bacterial Disease: | n/t | n/t |
| Fungal Disease | | |
| Anthracnose (*Collectotrichum* spp.): | n/t | n/t |
| Brown Root Rot or Corky Root (*Pyrenochaeta lycopersici*): | n/t | Susceptible |
| Collar Rot or Stem Canker (*Alternaria solani*): | n/t | Susceptible |
| Early Blight Defoliation (*Alternaria solani*): | Susceptible | Susceptible |
| Fusarium Wilt Race 1 (*F. oysporum f. lycopersici*): | Resistant | Resistant |
| Fusarium Wilt Race 2 (*F. oysporum f. lycopersici*): | Resistant | Resistant |
| Fusarium Wilt Race 3 (*F. oysporum f. lycopersici*): | Susceptible | Susceptible |
| Grey Leaf Spot (*Stemphylium* spp.): | n/t | n/t |
| Late Blight, race 0 | Susceptible | Susceptible |

TABLE 1-continued

Characterization of tomato variety 'H1776' compared to an industry standard, 'H5608'

| Character | H1776 | H5608 |
|---|---|---|
| (*Phytophthora infestans*) | | |
| Late Blight, race 1 | n/t | n/t |
| Leaf Mold race 1 (*Cladosporiom fulvum*): | n/t | n/t |
| Leaf Mold race 2 (*Cladosporiom fulvum*): | n/t | n/t |
| Leaf Mold race 3 (*Cladosporiom fulvum*): | n/t | n/t |
| Leaf Mold Other Races: | n/t | n/t |
| Nailhead Spot (*Alternaria tomato*): | n/t | n/t |
| Seporia Leaf spot (*S. lycopersici*): | n/t | n/t |
| Target Leaf spot (*Corynespora casiicola*): | n/t | n/t |
| Verticillium Wilt Race 1 (*V. dahliae* race 1): | Resistant | Resistant |
| Verticillium Wilt Race 2 (*V. dahliae* race 2): | n/t | Susceptible |
| Other Fungal Disease: | n/t | n/t |
| Insects and Pests | | |
| Colorado Potato Beetle (*L. decemlineata*): | n/t | n/t |
| Root Knot Nematode (*M.* sp.): | Resistant | Resistant |
| Spider Mites (*Tetranychus* spp.): | n/t | n/t |
| Sugar Beet Army Worm (*s. exigual*): | n/t | n/t |
| Tobacco Flea Beetle (*E. hirtipennis*): | n/t | n/t |
| Tomato Hornworm (*M. quinquemaculata*): | n/t | n/t |
| Tomato Fruit worm (*H. zea*): | n/t | n/t |
| Whitefly (*T. vaporariorum*): | n/t | n/t |
| Other: | n/t | n/t |

Chemistry and Composition of Full-ripe Fruits

TABLE 2

Hot-break tomato juice characteristics for new variety 'H1776' and two check varieties 'H5608' and 'H3402'

|  | 'H1776' | 'H5608' | 'H3402' |
|---|---|---|---|
| Serum viscosity (centistokes) | 13.8 | 10.8 | 7.9 |
| Juice Bostwick (cm) | 10.0 | 10.7 | 12.7 |
| Soluble solids (° Brix) | 5.6 | 5.1 | 5.5 |
| Lycopene (ppm) | 130 | 133 | 127 |
| Fruit Weight (gm) | 83 | 72 | 60 |

Average of 2 years of trials in California in a total of 30 tests from 25 locations.

TABLE 3

| Phenology | | | |
|---|---|---|---|
|  | 'H1776' | 'H5608' | 'H3402' |
| Fruiting Season | short | short | short |
| Relative Maturity | late | late | medium |

TABLE 4

| Adaptation | | | |
|---|---|---|---|
| | 'H1776' | 'H5608' | 'H3402' |
| Culture | Field | Field | Field |
| Principle use | concentrated | Whole-pack, Concentrated | Whole-pack, Concentrated |
| Machine harvest | Yes | Yes | Yes |
| Regions of adaptability | | | |
| California Sacramento Upper/SJ valley | Yes - 1 | Yes - 2 | Yes - 2 |
| California Lower SJ Valley | Yes - 2 | Yes - 1 | Yes - 3 |
| Northeastern USA | No | No | Yes - 1 |

If more than one category applies, they are listed in rank order.

Comparison to Closest Varieties

Data in Table 1, 3, and 4 are based primarily upon trials conducted in Collegeville, Calif. (USA) from two replications, non-staked, in a research plot environment. Comparisons among varieties for processing traits were done over two years of side-by side testing throughout California. Disease resistance and adaptability assessments are based upon numerous observations collected throughout California and in regions/climates with specific disease pressure for ripe fruit rots, bacterial spot, bacterial canker, early blight, and late blight, including Ontario (Canada).

Several characteristics can distinguish 'H1776' from the similar commercial variety 'H5608'. The fruit size of 'H1776' is significantly larger and wider than 'H5608'; 'H1776' is approximately 11 grams heavier than 'H5608'. Regarding processing characteristics, 'H1776' has a soluble solids level (in ° Brix) of about 0.5° Brix higher than 'H5608' and a thicker juice viscosity. Furthermore, 'H1776' also shows a slightly better resistance to ripe fruit rots.

Further Embodiments

Additional methods provided herein include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid. Accordingly, another aspect of the disclosure relates a method for producing an inbred tomato variety by: planting seed of the tomato variety 'H1776'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1776'. Tomato plants capable of expressing substantially all of the physiological and morphological characteristics of the parental inbred lines of tomato variety 'H1776' include tomato plants obtained by chasing selfs from seed of tomato variety 'H1776'.

One of ordinary skill in the art will recognize that once a breeder has obtained inbred tomato plants by chasing selfs from seed of tomato variety 'H1776', the breeder can then produce new inbred plants such as by sib-pollinating, or by crossing one of the identified inbred tomato plant with a plant of the tomato variety 'H1776'.

The disclosure further includes introducing one or more desired traits into the tomato variety 'H1776'. For example, the desired trait may include male sterility, male fertility, herbicide resistance, insect resistance, disease resistance, and drought resistance.

The desired trait may be found on a single gene or combination of genes. The desired trait may be a genetic locus that is a dominant or recessive allele. The genetic locus may be a naturally occurring tomato gene introduced into the genome of a parent of the variety by backcrossing, a natural or induced mutation, or a transgene introduced through genetic transformation techniques. For a genetic locus introduced through transformation, the genetic locus may comprise one or more transgenes integrated at a single chromosomal location. Accordingly, the disclosure provides tomato plants or parts thereof that have been transformed with one or more transgenes (i.e., a genetic locus comprising a sequence introduced into the genome of a tomato plant by transformation) to provide a desired trait. In one aspect, the one or more transgenes are operably linked to at least one regulatory element.

The gene(s) may be introduced to tomato variety 'H1776' through a variety of well-known techniques, including for example, molecular biological, other genetic engineering, or plant breeding techniques, such as recurrent selection, back-crossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) (also referred to as Microsatellites)), enhanced selection, genetic marker enhanced selection, and transformation. Accordingly, tomato seed, plants, and parts thereof produced by such genetic engineering or plant breed techniques are also part of the present disclosure.

Also provided herein are single locus converted plants and seeds developed by backcrossing wherein essentially all of the morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus). One or more locus conversion traits may be introduced into a single tomato variety.

Deposit Information

A deposit of the tomato varieties 'H1776' is maintained by HeinzSeed Company, having an address at 6755 CE Dixon St, Stockton, Calif. 95206, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the American Type Culture Collection, (ATCC), P.O. Box 1549, MANASSAS, Va. 20108 USA.

Applicants have made available to the public without restriction a deposit of at least 2500 seeds of tomato variety 'H1776' with the American Type Culture Collection (ATCC), P.O. Box 1549, MANASSAS, Va. 20108 USA, with a deposit on Dec. 12, 2017 which has been assigned ATCC number PTA-124677.

The deposits will be maintained in the ATCC depository, which is a public depository, for a period of 30 years, or 5 years after the most recent request, or for the effective life of the patent, whichever is longer, and will be replaced if a deposit becomes nonviable during that period.

What is claimed is:

1. Tomato seed designated as 'H1776', representative sample of seed having been deposited under ATCC Accession Number PTA-124677.

2. A plant produced by growing the seed of claim 1.

3. A plant part from the plant of claim 2, wherein the plant part comprises at least one cell from tomato variety 'H1766', and the plant part is selected from leaf, ovule, pollen, cell, rootstock, scion, fruit, cotyledon, meristem, anther, root, root tip, pistil, flower, stem, calli, stalk, hypocotyl, pericarp, and combinations thereof.

4. A tomato plant having all the physiological and morphological characteristics of the tomato plant of claim 2.

5. A plant part from the plant of claim 4, wherein the plant part comprises at least one cell from tomato variety 'H1766, and the plant part is selected from leaf, ovule, pollen, cell, rootstock, scion, fruit, cotyledon, meristem, anther, root, root tip, pistil, flower, stem, calli, stalk, hypocotyl, pericarp, and combinations thereof.

6. A tomato plant having all of the physiological and morphological characteristics of tomato variety 'H1776' listed in Table 1, wherein a representative sample of seed has been deposited under ATCC Accession Number PTA-124677.

7. A plant part from the plant of claim 6, wherein the plant part comprises at least one cell from tomato variety 'H1766', and the plant part is selected from leaf, ovule, pollen, cell, rootstock, scion, fruit, cotyledon, meristem, anther, root, root tip, pistil, flower, stem, calli, stalk, hypocotyl, pericarp, and combinations thereof.

8. Pollen of the plant of claim 2.

9. An ovule of the plant of claim 2.

10. A tissue culture of regenerable cells from the plant part of claim 3.

11. A tomato plant regenerated from the tissue culture of claim 10, the plant having all of the physiological and morphological characteristics of tomato variety 'H1776' listed in Table 1, wherein a representative sample of seed has been deposited under ATCC Accession Number PTA-124677.

12. A protoplast produced from the tissue culture of claim 10, wherein a plant regenerated from the protoplast has all of the physiological and morphological characteristics of tomato variety 'H1776' listed in Table 1.

13. A method of producing a tomato plant derived from tomato variety 'H1776', the method comprising crossing the plant of claim 2 with another tomato plant to produce a $F_1$ hybrid tomato plant.

14. The method of claim 13, further comprising harvesting seed from the $F_1$ hybrid tomato plant.

15. The method of claim 13, further comprising crossing the $F_1$ hybrid tomato plant with itself or another plant to produce seed from a progeny plant.

16. A plant having all the physiological and morphological characteristics of the plant of claim 2, further comprising a transgene.

17. A plant having all the physiological and morphological characteristics of the plant of claim 2, further comprising a single locus conversion.

18. A method of making seeds from tomato variety 'H1776', the method comprising selecting seeds from a cross of one 'H1776' plant with another 'H1776' plant, a sample of 'H1776' tomato seed having been deposited under ATCC Accession Number PTA-124677.

19. A method for producing a tomato fruit, the method comprising:
    growing the tomato plant of claim 2 to produce a tomato fruit; and
    harvesting the tomato fruit.

20. A method for producing a tomato seed comprising:
    self-pollinating the tomato plant of claim 2; and
    harvesting the resultant tomato seed.

21. A method of vegetatively propagating the plant of claim 2, the method comprising:
    obtaining a part of the plant; and
    regenerating a plant from the part, the regenerated plant having all of the physiological and morphological characteristics of tomato variety 'H1776' listed in Table 1.

* * * * *